United States Patent
Baker

Patent Number: 5,954,670
Date of Patent: Sep. 21, 1999

[54] MANDREL-GUIDED TANDEM MULTIPLE CHANNEL BIOPSY GUIDE DEVICE AND METHOD OF USE

[76] Inventor: Gary H. Baker, 1966 Loop Rd., Fortuna, Calif. 95540

[21] Appl. No.: 09/030,869

[22] Filed: Feb. 26, 1998

Related U.S. Application Data

[63] Continuation-in-part of application No. 08/702,783, Aug. 23, 1996, abandoned, which is a continuation-in-part of application No. 08/318,906, Oct. 5, 1994, abandoned.

[51] Int. Cl.[6] ....................................................... A61B 5/00
[52] U.S. Cl. ............................................................. 600/567
[58] Field of Search ..................................... 600/434, 562, 600/564–568

[56] References Cited

U.S. PATENT DOCUMENTS

| | | |
|---|---|---|
| 4,230,123 | 10/1980 | Hawkins, Jr. . |
| 4,539,976 | 9/1985 | Sharpe . |
| 4,616,656 | 10/1986 | Nicholson et al. . |
| 4,651,753 | 3/1987 | Lifton . |
| 4,850,373 | 7/1989 | Zatloukal et al. . |
| 4,881,551 | 11/1989 | Taylor . |
| 4,907,599 | 3/1990 | Taylor . |
| 5,011,473 | 4/1991 | Gatturna . |
| 5,012,818 | 5/1991 | Joishy . |
| 5,018,530 | 5/1991 | Rank et al. . |
| 5,056,529 | 10/1991 | de Groot . |
| 5,078,142 | 1/1992 | Siczek et al. . |
| 5,107,843 | 4/1992 | Aarnio et al. . |
| 5,111,828 | 5/1992 | Kornberg et al. . |
| 5,183,052 | 2/1993 | Terwilliger . |
| 5,183,054 | 2/1993 | Burkholder et al. . |
| 5,193,533 | 3/1993 | Chin et al. . |
| 5,219,351 | 6/1993 | Teubner et al. . |
| 5,234,000 | 8/1993 | Hakky et al. . |
| 5,263,928 | 11/1993 | Trauthen et al. . |
| 5,357,978 | 10/1994 | Turk . |
| 5,395,317 | 3/1995 | Kambin . |
| 5,526,822 | 6/1996 | Burbank et al. . |
| 5,649,547 | 7/1997 | Ritchart et al. . |

*Primary Examiner*—Max Hindenburg
*Attorney, Agent, or Firm*—Depaoli & Frenkel, P.C.

[57] ABSTRACT

A biopsy guide device and method for obtaining multiple biopsies at a target area without having to withdraw the biopsy guide device from the target area and reinsert the device. The biopsy guide device contains at least one means for receiving a biopsy obtaining instrument and a means for guiding the biopsy guide device to the target area. The biopsy guide device is secured internally at the target area by a guide mandrel. The biopsy guide device can be rotated about the guide mandrel to obtain multiple biopsies of the target area.

21 Claims, 3 Drawing Sheets

MANDREL-GUIDED TANDEM MULTIPLE CHANNEL BIOPSY GUIDE DEVICE AND METHOD OF USE

The present application is a Continuation-In-Part application of U.S. application Ser. No. 08/702,783 filed Aug. 23, 1996 now abandoned which is a Continuation-In-Part of U.S. patent application Ser. No. 08/318,906 filed Oct. 5, 1994, now abandoned.

BACKGROUND OF THE INVENTION

1. Field of the Invention

The present invention is directed to an improved biopsy guide device and a method used for positioning the biopsy guide device in a subcutaneous target for percutaneous biopsy. More specifically, the present invention is directed to an improved needle biopsy guide device and method of use thereof in obtaining multiple biopsies within a target area.

2. Description of the Prior Art

It has become common to take samples of inner tissues from men and animals with devices which pass through the skin. Tissue samples taken in this manner are used to diagnose various diseases such as cancer without resorting to open surgery. Guidance by medical imaging becomes useful when targets are not adequately localized by external palpation. For example, a great importance is placed on the use of mammography for the early diagnosis of breast cancer. Early intervention appears to alter the outcome of the disease. Mammography screening detects small suspicious areas within the breast before they are palpable by a physician or by the patient. However, for most of these suspicious areas, mammography cannot distinguish malignant tissue from benign tissue. This shortcoming of mammography often precipitates a biopsy. Most suspicious abnormalities are benign if biopsied. The patient with a suspicious area on a mammogram must decide between the worry of waiting and watching versus the pain, disfigurement and cost of open surgical biopsy. A by-product of mammography, this problem is common and costly to society in health care dollars, suffering and litigation.

The method for making a definitive diagnosis of breast cancer is by microscopic examination of the suspect tissue. Accurate techniques less costly than open surgical biopsy to obtain samples of suspicious tissue for microscopic examination are desired. For example, core needle biopsy devices which pass through the skin guided by stereotactic mammography or ultrasound can accurately sample suspicious targets and have become popular alternatives to open biopsy. Recent studies suggest that tissue cores obtained using a stereotactic mammographically guided biopsy with large 14 gauge needles are equal in microscopic diagnostic accuracy to open surgical biopsy. However, as many as 5 to 15 biopsy specimens are currently considered usual and necessary for large core needle biopsies of mammary glands.

Alternatively, breast sonography can be used for large needle core biopsy guidance instead of stereotactic mammography in 25–35% of suspicious breast abnormalities. Both stereotactic mammography and breast sonography are being commercialized with vigor as a replacement for open surgical biopsy, touting reductions in cost, waiting period and breast disfigurement.

Stereotactic mammographic guided biopsy requires costly equipment and costly floor space which are new expenses. The invention herein eliminates the need for stereo guidance.

Another problem with stereotactic mammography is the possibility of needle track seeding with malignant cells. Needle track seeding with malignant cells after undergoing only 5 large stereotactic needle biopsies has been documented histologically in a mammary gland which was later surgically removed for cancer (Harter L. P. et al., Radiology 1992; 185:713–714).

Most stereotactic biopsy units operate preferentially with the needle perpendicular to and directed toward a compression paddle or film holder. This is the shortest dimension of a breast flattened by compression paddles. Unfortunately, small breasts or targets near the deep skin surface run the risk of biopsy needle penetration of the far side skin causing impact damage to equipment (bucky bashing). Short throw biopsy needles can be employed but are known to provide inferior tissue specimens compared to long-throw needles. Also, a strict long-term stable relationship is required between the patient and the needle. Also, patient movement between stereotactic calculations and needle placements send the needle to a former target location. The intrinsic mobility of suspicious targets in soft breast tissue result in glancing tangential target misses because the target moves off to the side during needle thrust.

Percutaneous cannula guides have been used to guide biopsy devices to the target tissue for repeated sampling. These are coaxial in design. The cannula goes to or toward the abnormality, but not through it. The biopsy needle passes through the guide cannula. Coaxial guide cannulas present only one trajectory through the tissue target until redirected by new imaging guidance. Coaxial devices for biopsy do not internally immobilize the target. Since coaxial devices provide only alignment to the target, patient motion, cannula motion or tangent target displacement can result in a misdirected biopsy.

Coaxial external needle guides, some employing cannulas, have been used to hold and guide percutaneous breast biopsy needles (Siczek et al. U.S. Pat. No. 5,078,142, and Aarnio et al. U.S. Pat. No. 5,107,843). Most of those external guides require stereotactic positioning. One such device includes a combination of external and percutaneous guides (Teubner et al., U.S. Pat. No. 5,219,351). Part of Teubner's stereotactic guided device is called a needle in his patent, but it is a percutaneous guide cannula. It is coaxial and stereotactic, and suffers from most of the drawbacks of such method. Teubner et al. solve one of the stereotactic biopsy problems (difficulties with targets in thin breasts or those lying near the posterior skin surface) by allowing the biopsy needle the freedom to angle away from perpendicular-to-image-receptor and offer improved choice of puncture site. Teubner's coaxial stereotactic guided device is expensive and patient access to it is limited. The external guide devices are distant from the target and subject to needle trajectory deflection and to patient or target motion.

Such disadvantages are also true for the multi-lumen biopsy cannula designed by Zatloukal et al. (U.S. Pat. No. 4,850,373). Zatloukal retains coaxial design, presenting only one trajectory through target tissue for repeated biopsies unless the whole cannula is repositioned. The multi-lumen biopsy cannula of Zatloukal et al. has a circular cross-section outer cannula that contains a close fitting inner biopsy cannula with its circular cross section flattened on one side less than ⅓ its maximal diameter producing a ⅓ moon-shaped second lumen between the inner and outer cannulas. The quarter-moon-shaped extra lumen is not designed for the purpose of the transmission of guide pins, fixation wires or other sampling devices. The extra lumen was designed for the injection of substances such as blood coagulation substances, vasoactive drugs and the like to the target site.

The cannulas are coaxial but are not joined. One is free to rotate inside the other, thereby failing to provide a predictable orbit for the biopsy channel around an axle mandrel in the target. Thus, the coaxial cannulas do not allow the biopsy channel to appose a new locus on the target as in the present invention later described.

Multiple cannulas or tandem multichannel devices, joined side-to-side inside and outside the body, where target guidance and internal fixation is the purpose of one cannula while the other cannula is used for biopsy, as in the present invention, have not appeared in the medical or patent literature.

Kambin (U.S. Pat. No. 5,395,317) discloses a device with tandem channels and a mandrel guidance. Kambin employs one channel for coaxial mandrel guidance and use of the same channel for intervertebral disectomy after removing the mandrel during the surgical procedure. A tandem channel for endoscopy follows the first channel and is not permanently joined. Kambin employs a jig as a means to join and to guide the second tandem cannula alongside the first image-guided cannula. The joining means jig is entirely external to the body. The joining means jig in Kambin does not provide a solid permanent joining, and the joining means does not penetrate into subcutaneous tissues and therefore rotation or withdrawal or insertion forces applied to one cannula do not predict the behavior of the movement of the other cannula. Also, external forces on the proximal ends of both cannulas do not predict the behaviors of the internal distal ends of both cannulas.

The Biopsys Mammotome (U.S. Pat. No. 5,649,547) is a tandem joined multiple channel biopsy device. The Biopsys Mammotome uses one channel for suction and one channel for mechanized biopsy, relies on external positioning devices and not internal fixation devices, requires strict breast immobilization and stereotactic guidance or sonographic guidance. The patent alleges that the device rotates about its biopsy channel. (see also Biopsys Mammotome, Mark Ritchart, John Wardle, Fred Burbank MD et al. Biopsys Medical, Inc. Biopsys Medical, Inc (Premier Laser), 3 Morgan, Irvine, Calif. 92718).

Kornberg (U.S. Pat. No. 5,111,828) shows guidance over a mandrel, orthogonal imaging and target anchoring. However, closer inspection discloses a percutaneous excisional breast biopsy device having the following deficiencies: (1) non-removable anchor, (2) a slender hook-wire which should not be followed forward over (manufacturer warnings; existing litigation related to post-surgical retained hook wire); (3) one time biopsy; (4) orthogonal images all completed before device insertion; (5) guide sleeve and hook wire removed by single biopsy; (6) excisional biopsy; and (7) unsuitable for lesions over 20 mm.

Stylets, wires, pins and mandrels have been used as guide devices for biopsy. Previous to Kambin (U.S. Pat. No. 5,395,317) such guide devices have been a part of coaxial systems. The mandrel is removed after a cannula device has been positioned over it, since the cannula would be difficult or impossible to use while the guide mandrel occupies its channel. Coaxial guide mandrels are good for only one tissue sample. Coaxial guide mandrels must be repositioned by using medical imaging if additional mandrel-guided samples are desired. Kambin also withdraws his guide mandrel because he has other uses for both of his channels. An ingenious large "stylet", designed with a central channel to follow over a guide mandrel, shown in the breast biopsy device of Kornberg et al. (U.S. Pat. No. 5,111,828) is coaxial, but can only obtain one biopsy with each guide placement. The size of the Kornberg device required for excision makes his procedure painful and is as difficult as open biopsy for larger targets, especially in patients with tough, fibrous breasts.

Although there are a number of biopsy devices in the medical and surgical industry, there is still a need for a biopsy guide device that can provide multiple biopsies from a subcutaneous target area.

SUMMARY OF THE INVENTION

The present invention is directed to a biopsy guide device and a method for positioning the biopsy guide device in a subcutaneous target area. The method provides for multiple biopsies from multiple precisely measurable foci within the subcutaneous target area without having to withdraw the guide device. Positioning the biopsy guide device at the subcutaneous target area is image-guided and suitable to most forms of medical imaging such as stereotactic x-ray mammography imaging, medical diagnostic ultrasound, computed x-ray tomography, or magnetic resonance imaging, but also by conventional orthogonal images produced by x-ray, mammography or nuclear medical imaging. The present invention solves the problem of having to purchase expensive stereotactic mammography equipment for percutaneous needle biopsies when a suspicious subcutaneous target can be localized only by mammography. Ubiquitous non-stereotactic dedicated mammography units are sufficient.

The biopsy guide device of the present invention is a multiple channel biopsy guide that is comprised of a plurality of tandem channels or cannulas joined permanently side-to-side. One cannula is employed to guide the device to a subcutaneous target area. At least one additional cannula is employed to receive and guide a biopsy obtaining device to the target area to obtain a biopsy.

A biopsy is obtained by internally transfixing a guide mandrel through the subcutaneous target. The guide channel of the tandem multiple channel biopsy guide device is placed over the guide mandrel. The guide channel follows the guide mandrel through intervening tissue toward the target area transfixed by the guide mandrel. One or more biopsy channel(s) of the tandem multiple channel biopsy guide device is used to receive a biopsy device to obtain a biopsy. The biopsy channel can be rotated about the target-transfixing guide mandrel to obtain biopsies from new foci at the target area without having to withdraw the device since the guide mandrel anchors the device at the target area.

Confident repositioning inside the target area is permitted by the rigidness of the guide device and by the guide mandrel confined inside but protruding substantially beyond the biopsy guide device to internally transfix the target area and prevent the target from separating from the biopsy guide device.

The primary object of the present invention is to provide mandrel guided positioning of the biopsy guide device and internal fixation to a subcutaneous target that will: (1) provide for multiple percutaneous biopsies from a single puncture; (2) use commonly known guidance techniques; and (3) require commonly owned medical imaging equipment eliminating the need for stereotactic mammographic imagining equipment. The present invention device and method of use provides precise target biopsy using standard orthogonal mammographic, nuclear, or x-ray imaging, as well as by using sonography or computed tomography. Innumerable facilities exist with standard dedicated mammography and medical sonography and nuclear medical and computed tomography equipment. Thousands of radiologists have learned to perform pre-biopsy needle localizations of non-palpable breast targets for subsequent open surgical biopsy by their surgeon colleagues. The method herein is similar. Stereotactic mammography units are still uncommon and require special training.

An additional object is to reduce societal expenditures while increasing early breast cancer detection by providing a disposable, low cost biopsy device that requires no stereotactic imaging equipment purchase, shortens procedure time and eliminates over-utilization and under-utilization brought about by equipment or procedure price incentives.

Yet a further object is to enable multiple tissue samples to be obtained from several adjacent sites within or very near the tissue biopsy target avoiding repeat repenetration of skin and intervening normal tissues.

Still a further object is to provide internal fixation between the multiple channel biopsy guide device and guide mandrel and the tissue biopsy target so that the relationships between the device and target remain stable during patient movements and so that a target in soft pliable breast tissue cannot slip out of the path of the guide device during tissue sampling action.

A further object is to enable retrieval of multiple needle biopsy specimens via the inside of the device's biopsy channel to decrease the potential to seed malignant cells or bacteria compared to a needle track that passes through normal intervening tissue.

Even a further object is to only employ long-throw biopsy needles since short-throw needles demonstrate inferior function and require the considerable expense of owning and stocking separate short-throw equipment.

Another object is to prevent the mandrel from backing out or falling out and to prevent the target from slipping off the mandrel.

Yet still another object is to provide a joining means between two cannulas of the device to form a completely solid one piece tandem multichannel guide.

Still further objects and advantages will become apparent from a consideration of the following description and drawings.

DETAILED DESCRIPTION OF THE INVENTION

Figure 1:
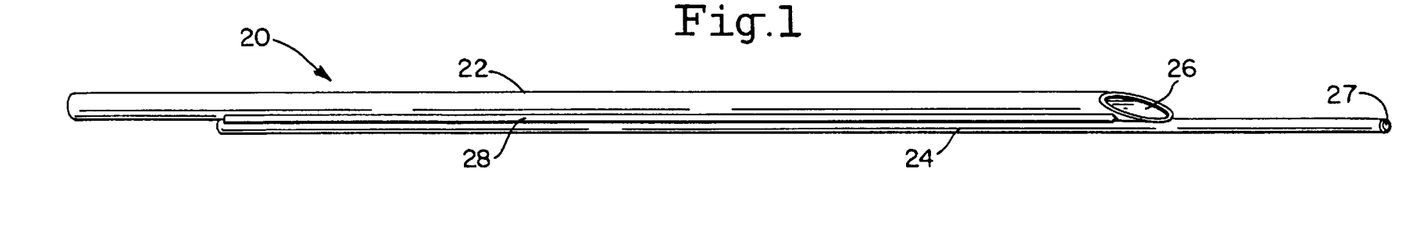
FIG. 1 is a side view of the biopsy guide device composed of the side-by-side biopsy channel member and the guide channel member.
Figure 3A:
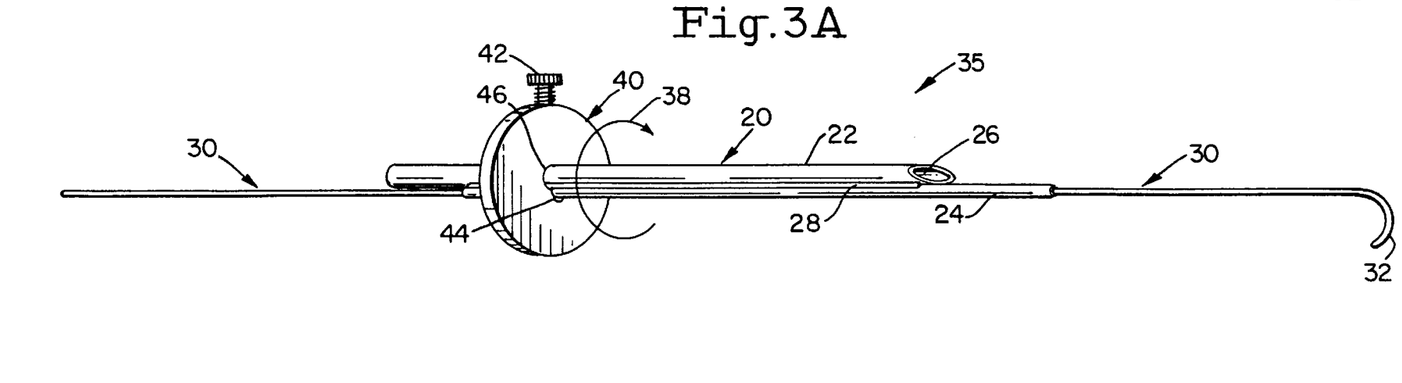
FIG. 3A is a side view of the multiple channel biopsy guide device assembly.

The present invention is directed to a biopsy guide device and method of using the device. Referring to FIGS. 1 and 3, the biopsy guide device 20 is composed of at least two tandem cannulas or channels permanently joined together at their distal and proximal ends. One cannula 24 serves as a guide means for receiving a guide mandrel 30. Guide mandrel 30 is passed through lumen 27 of guide cannula 24. At least one cannula 22, including lumen 26 serves as a biopsy means for receiving a biopsy obtaining instrument, i.e., long throw biopsy needle (not shown), for acquiring percutaneous biopsies.

The tandem multiple channel biopsy guide device 20 is designed to be left at the target site as long as desired. Internal fixation of the target pierced by a guide mandrel 30 prevents a change in relationship between the target and the device 20. The off-set axis of the biopsy cannula 22 relative to guide cannula 24 allows new portions of the target to be sampled as the biopsy guide device 20 is rotated around the axle formed by the guide mandrel 30 which secures the biopsy guide device to the target site. Thus, multiple percutaneous biopsies can be obtained at different radial sites in the target area without removing the device or re-imaging the target site. Biopsy guide device maneuvers can be made without concern for changing the relationship to the target. The guide mandrel 30 in the guide mandrel cannula 24 provides for a secure internal fixation of the biopsy cannula to the target site by transfixing the target to allow orthogonal image-guided positioning device manipulations, patient movements and additional interactions without the need for repeated imaging.

Again, referring to FIGS. 1 and 3, one embodiment of the tandem multiple channel biopsy guide device 20 is shown. The tandem multiple channel biopsy guide device 20 is composed of a biopsy cannula 22 and a guide cannula 24, each containing respective central lumens 26 and 27. The biopsy cannula 22 is permanently joined in tandem with the guide cannula 24 by a joining means 28. The joining means 28 travels with the tandem multichannel biopsy device into subcutaneous tissue and ensures that the distal biopsy cannula remains directly beside the guide cannula which in turn contains the guide mandrel 30. The joining means 28 and, thus, the permanent joining of biopsy cannula 22 with guide cannula 24 offers the advantage that rotational or push/pull movements applied externally to the proximal ends of the cannulas where the cannulas are visible to the naked eye predicts the non-visible movement of the internal distal ends of the cannulas when the biopsy guide device is inserted into the target area. The joining means 28 can be any suitable material such as an adhesive, a welding or any suitable chemical or mechanical binder that joins the cannulas together.

Figure 2:
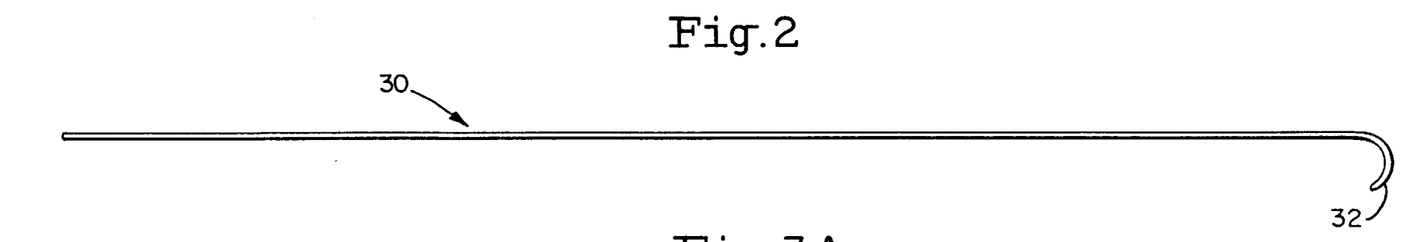
FIG. 2 is a side view of an anchor guide mandrel with a J-hook distal configuration.

Many kinds of guide mandrels 30 can be employed to secure the biopsy guide device of the present invention to the target site. For example, aciculate guide mandrels of varying diameter can be used. Very narrow diameter guide mandrels may require passage of a small stiffening, single lumen cannula thereover before the narrow mandrels are strong enough to serve as guides for larger cannulas. Such single lumen cannulas may have a beveled distal end to prevent tissue coring when the single lumen cannula is initially inserted at the target site. FIG. 2 shows an anchor guide mandrel 30 with a distal J-hook 32. The anchor guide mandrel 30 transfixes the subcutaneous target area and secures the biopsy guide device internally to the target area by sliding the guide cannula 24 over the anchor guide mandrel 30. The guide mandrel 30 is approximately 2½ times the length of the tandem multiple channel biopsy guide device 20 shown in FIG. 1. As shown in FIG. 3A, the mandrel 30 protrudes out of the guide channel cannula 24. The portion of guide mandrel 30, such as J-hook 32, anchors device 20 and prevents target escape.

Another anchoring ramification uses a straight mandrel with an aciculate distal end to pierce through the entire breast so that it can be externally held on both sides of the breast. The proximal end is secured by a removable hub. The removable hub can be designed to fit the small aciculate mandrels, the anchor guide mandrels 30, the single lumen exchange cannula, and the proximal end of the biopsy channel 22. The removable hub can include a large cylindrical partial lumen at one end which penetrates the removable hub midway through the hub that fits over cannulas. A small cylindrical lumen at the end opposite to the large cylindrical partial lumen penetrates the removable hub to join the larger diameter partial lumen. The small cylindrical complete lumen fits over the mandrels. A set screw which fits into a screw hole perpendicular to the large cylindrical partial lumen and the small cylindrical complete lumen helps keep the cannulas in place while in the hub.

For use in achieving a percutaneous biopsy, biopsy guide device 20 is present as an assembly 35 as shown in FIG. 3A. Thus, biopsy guide device 20 comprises a multichannel, side by side guide mandrel cannula 24 and a biopsy cannula 22 connected at their proximal and distal ends by joining means 28. In assembly, an anchor guide mandrel 30 is supported in lumen 27 of cannula 24, see FIG. 1. In actual use, the anchor guide mandrel 30 is first inserted into body tissue and cannula 24 is slid over the anchor guide mandrel 30 into the body tissue. To perform the biopsy, any type of useful needle biopsy device is passed through lumen 26 of biopsy cannula 22, the sample taken and the biopsy needle with sample withdrawn back through cannula 22. Importantly, multiple biopsy samples can be taken through the biopsy cannula 22 as the biopsy cannula is rotated about the anchor guide mandrel 30 as shown by arrow 38 without the removal of the multichannel biopsy guide device from the body tissue.

Figure 3B:
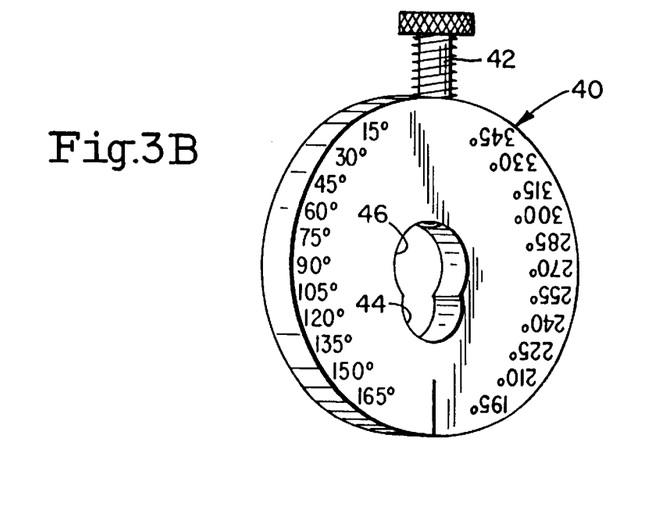
FIG. 3B is a perspective view of a depth-penetration stop used in the assembly of FIG. 3A.

FIGS. 3A and 3B show that assembly 35 can include a depth-penetration stop 40, slidable on the outside of the tandem multiple channel biopsy guide device 20. The depth-penetration stop 40 contains a hole side lobe 44 that is designed to fit over a guide channel 24 and another hole 46 that is sized for a biopsy channel 22. The depth penetration device 40 prevents inadvertent longitudinal movement, i.e., advancement, or rotation of the prepositioned tandem multiple channel biopsy guide device 20 and allows return to exact prepositioning if device 20 is inadvertently or intentionally moved or rotated. A set screw 42 is tightened to fix depth-penetration stop 40 to the multiple channel biopsy guide 20 at any position up and down its length. Tightening set screw 42 when the depth penetration stop 40 rests against the skin provides a visible marker of depth of penetration throughout the method and prevents penetration beyond the chosen depth. The depth-penetration stop 40 can be imprinted on at least one face with a radial dial such as in degrees to improve positioning accuracy. Thus, the biopsy guide device 20 can be precisely positioned radially at the target area depth to obtain the desired specimens. If moved, multiple channel biopsy guide device 20 can be restored to its position in the target exactly with or without additional imaging guidance.

Figure 4A:
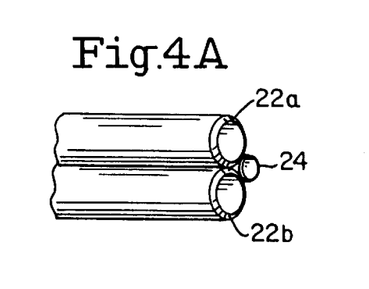
FIG. 4A is a side view of the distal end of an alternative tandem multiple channel biopsy guide device showing two biopsy channel members and a single guide channel member joined to both biopsy channel members.
Figure 4B:
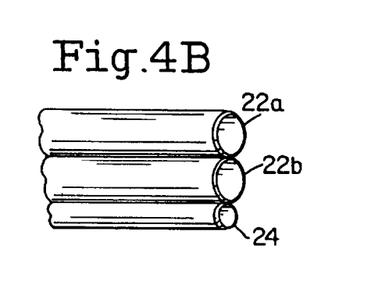
FIG. 4B is a side view of the distal end of a tandem multiple channel biopsy guide device showing a variation of the device of FIG. 4A where the guide cannula member is joined to one of two biopsy channels.
Figure 4C:
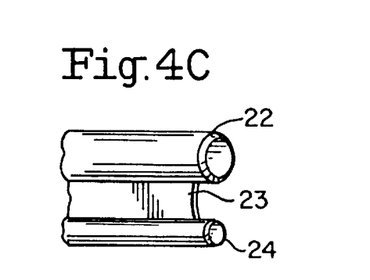
FIG. 4C is a side view of the distal end of another alternative tandem multiple channel biopsy guide device with a spacer between the biopsy channel member and the guide channel member.
Figure 4D:
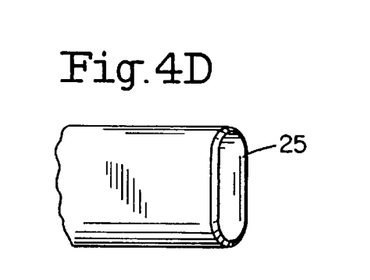
FIG. 4D is a side view of the distal end of a cannula for retaining both a biopsy needle and guide mandrel.
Figure 4E:
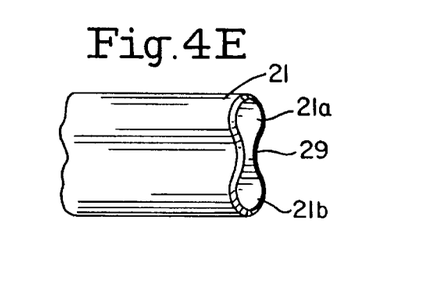
FIG. 4E is a side view of the distal end of a cannula showing a variation of the cannula of FIG. 4D where an indention separates the cannula into two channels.

FIG. 4A through FIG. 4E depict variations and ramifications on the basic invention concept. Any suitable variation for securing the biopsy cannula 22 to the guide mandrel 30 can be employed. Any configuration which will allow the biopsy cannula 22 to rotate around the guide mandrel 30 is preferred. Initially, variations of the lengths and overlap of joined cannulas, including off-parallel configurations are within the scope of the present invention. FIGS. 4A–E show how cannulas can be joined and shaped into various multiple functional channel designs and be included within the scope of this invention. FIG. 4A shows two tandem biopsy cannulas 22A and 22B with a guide mandrel cannula 24 joined to each of the biopsy cannulas 22A and 22B. FIG. 4B shows two tandem biopsy cannulas 22A and 22B and one guide mandrel cannula 24 secured to one of the biopsy cannulas in the same plane as cannulas 22A and 22B. FIG. 4C shows a biopsy cannula 22 joined in tandem to a guide mandrel cannula 24 by means of a mechanical spacer 23. FIG. 4D shows a single cannula 25 having sufficient internal space to retain at least one biopsy needle and at least one guide mandrel. FIG. 4E shows a variation of the cannula of FIG. 4D where the cannula 21 has a central indention 29 separating the cannula into sectional lobes 21A and 21B for a biopsy needle and a guide mandrel, respectively.

Although not shown, other configurations of tandem biopsy and guide structures can be considered part of the present invention. For example, one or more biopsy channel (s) can be joined permanently to the guide mandrel. Another variation on the mandrel guided multiple channel biopsy device 20 is a guide channel joined permanently in tandem with the biopsy obtaining instrument or biopsy gun. Also, a loop snare attached to the biopsy cannula 22 rather than a guide channel cannula can be used as a joining means to join the guide mandrel 30 to the biopsy cannula 22. Other variations and configurations for joining the biopsy and guidance means within the concept of this invention would be familiar to those skilled in the art. Additionally, variations in guide mandrel designs are within the scope of this invention. Thus, besides acicular and J-hook distal configurations, Y-hook, threaded screw and even spiral distal variations, among others can be used.

This invention is directed to a medical biopsy guide device and method for positioning the medical biopsy guide device in a subcutaneous target area. The device and method of this invention provide for biopsies from multiple precisely measurable foci within the target area.

The method for positioning the biopsy guide device is image-guided and suitable to most forms of medical imaging such as stereotactic x-ray mammography, medical diagnostic ultrasound, computed x-ray tomography, or magnetic resonance imaging, but also to conventional orthogonal images produced by x-ray, mammography or nuclear medical imaging. Common non-stereotactic mammography units are expected to provide the bulk of the imaging guidance for the method using the instant device. Thus, the need to purchase expensive stereotactical mammography equipment for percutaneous needle biopsy can be avoided.

In accordance with a method of use of the biopsy guide device of this invention, two 2-dimensional images are made of the subcutaneous target approximately orthographically. The images are combined to give a three-dimensional position of the subcutaneous target area.

Image 1 guides an introducer mandrel and subsequently the anchor guide mandrel 30 through the target. Orthogonal image 2 provides depth positioning for multiple channel biopsy device 20, following slidably along the shaft of the anchor guide mandrel 30. Referring again to FIG. 3, the target position is precisely maintained by internally fixing the target area by guide mandrel 30, and by precise depth and radial positioning of tandem, multiple channel biopsy guide device 20 over guide mandrel 30, as follows:

(a) A first x-ray view of a breast or other tissue is used to position a stiff guide mandrel 30 exactly on a line of the x-ray beam to the two-dimensional view and passing through the target area. Positioning of the guide mandrel 30 may be facilitated by first employing small mandrels and a single lumen exchange cannula as an introductory set for introducing the guide mandrel 30 to and through the target site.

(b) The multiple channel biopsy guide device 20 is inserted, confined in trajectory in reference to the first view as it pierces skin and tissue by following its guide channel 24 over the guide mandrel 30.

(c) A second x-ray view is taken approximately perpendicular to the first view projecting an elongate view of the guide mandrel 30. The guide channel 24 of the multiple channel biopsy device 20 is advanced over the guide mandrel 30 until the distal tip of the biopsy channel 22 is positioned on the line of the x-ray beam that passes through the target area on the two-dimensional second view.

(d) Biopsy channel 22 of the multiple channel biopsy guide device 20 delivers a biopsy needle to the target area.

(e) The biopsy needle is measurably positioned relative to the biopsy channel 22 and to the target area for the performance of the biopsy.

(f) After the performance of the initial biopsy, the multiple channel biopsy guide device 20 is rotated by an exact amount around guide mandrel 30 axle for exposure of biopsy channel 22 to a new radial point on the target area.

(g) Confident repositioning inside the target area is permitted by a rigidness bestowed by proximal and distal joining of the tandem channels 22 and 24 of the multiple cannula biopsy guide device 20 and by the guide mandrel 30 confined inside but protruding substantially beyond the guide cannula 24 to internally transfix the target area and to prevent the target from separating from the multiple channel biopsy guide device 20 during its rotation.

(h) Additional biopsy specimens are obtained at each new radial site.

Employing several small guide pin mandrels to initially locate the target area improves the odds for a direct hit on the target, benefiting the patient by the small size thereof and by shortening the time to target transfixation. Small in diameter, the pin mandrels must be strengthened by following one or more slightly larger introductory cannulas over the pin mandrel. A single introductory cannula or tissue dilator cannula can then follow over the combination. Such an introductory cannula is relatively thin-walled with a beveled distal end in contrast to the tissue dilator cannula. The tissue dilator cannula is thick-walled with a tapered distal end. Such thick-walled tissue dilator cannulas are employed when the tissue to be penetrated is tough and fibrous.

Figure 5A:
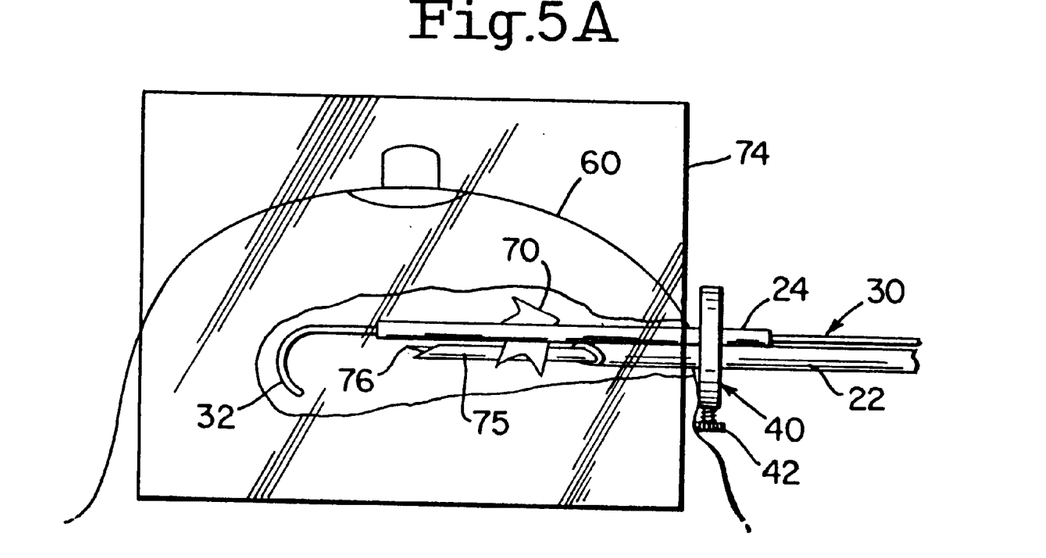
FIG. 5A is a craniocaudad view of the biopsy guide device assembly at the target area.
Figure 5B:
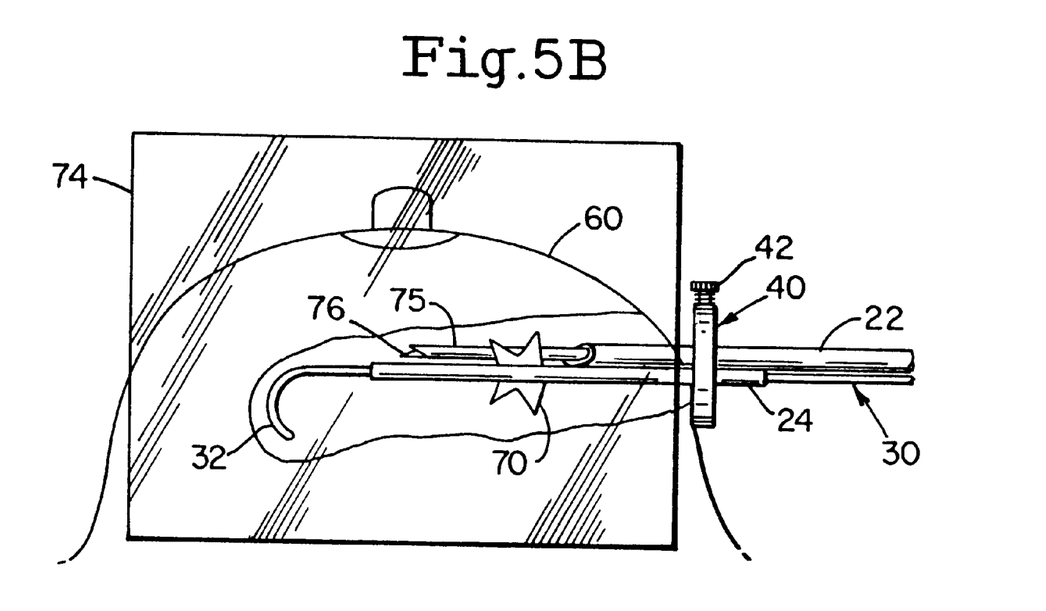
FIG. 5B is a craniocaudad view of the biopsy guide device assembly at the target area rotated 180° from the position of FIG. 5A.

In one embodiment, a bayonet relationship between the biopsy channel 22 and the guide channel 24 provides smaller lumen guide channel 24 as a leader to follow the mandrel 30 to the target, dragging the larger biopsy channel 22 through tissue as shown in FIGS. 5A and 5B.

Tissue sampling is performed just outside the distal end of the biopsy cannula 22 alongside bayonet guide cannula 24. The guide cannula 24 covers and strengthens the mandrel 30 in the tissue biopsy cutting area eliminating the possibility of transection.

As previously noted, the depth-penetration stop 40 prevents inadvertent advancement or rotation of the pre-positioned tandem multiple channel biopsy guide device 20 and allows return to exact pre-positioning if the tandem multiple channel biopsy guide device 20 is inadvertently or intentionally withdrawn or rotated.

The method of use of the device of this invention for mammography-guided breast biopsy can be described with reference to FIGS. 5A and 5B. The patient is preferably sitting up or lying on her side. A breast 60 containing a tissue target abnormality shown as star-shaped lesion 70 is placed in between the flat top surface of the mammography film holder and the mammography compression paddle. The compression paddle is fenestrated to permit needle placement into the breast while the breast is held under the paddle. The top compression paddle contains a grid for guidance purposes. The grid is visible on the paddle holding down the breast and also on the film image of the breast where the target 70 can be seen.

While the breast is held in compression, begin the method by exposing a first mammography film visualizing the target relationship to the grid image on the fenestrated paddle. A mark is placed on the skin of the breast 60 corresponding to the grid location of the target on the film. The method continues with the placement of a diamond-tip or aciculate pin mandrel designed to pass without deflection through skin, through tissues, and through the target lesion 70. The pin mandrel is aimed at target 70 by following the path of the x-ray beam that passed through the target 70 on the first mammography view. Small mandrels encourage deployment of more than one, increasing the odds of a direct hit on the target area. A second image positioned the same as the previous image confirms successful penetration of the target by at least one of the mandrels. If necessary, some or all of the guide mandrels are repositioned until target 70 is successfully penetrated. The best positioned mandrel is left in situ. The others are all removed. Small mandrels must be strengthened by placing small cannulas over them until they are stiff enough to guide a single lumen introductory cannula or a tissue dilator cannula to the target area. The single lumen introductory cannula follows over the strengthened pin mandrel to and through the target 70. Once the introductory cannula is deeply placed, the straight guide pin mandrel is removed and replaced by anchor guide mandrel 30 containing a distal flexible J-hook 32. The J-hook 32 is pushed out the distal end of the introductory cannula and the J-hook reforms its distal J-hook anchor configuration 32. The target 70 is now firmly transfixed and known to be located on the anchor guide mandrel 30, even if the target or patient moves. The introductory cannula may then be removed leaving behind the anchor guide mandrel 30.

The curved J-hook 32 on the distal end of the guide mandrel 30 is one embodiment of the guide mandrel configuration of this invention. As previously stated, the distal portion of guide mandrel 30 can be substituted with a solid, straight mandrel (guide pin) with a distal aciculate tip, a threaded distal tip, a branching Y-tip a corkscrew tip on a retractable barb tip, among other distal configurations.

A tissue dilator cannula may be used in place of the single lumen introductory cannula or may be used later to pass slidably over the anchor guide mandrel 30 to produce a tunneled out space in tough fibrous breasts for passage of the tandem multiple channel biopsy guide device 20.

Compression is released, the patient is removed for a brief rest and placed again in compression after the mammography tube has been repositioned to aim approximately 90 degrees from its initial x-ray trajectory. The fenestrated compression paddle is replaced with a small compression paddle 74 to facilitate access to the puncture site. The long shaft of the anchor guide mandrel 30 is now approximately parallel to the image plane where its whole length is visible on the third medical image. The penetration distance from the skin to reach the target 70 is measured from the third image.

A stylet with a proximal hub is placed inside the biopsy cannula 22 of the tandem multiple channel biopsy device 20 to prevent clogging of the lumen during transmission through intervening tissue. The stylet (not shown) is solid with a beveled distal end. The hub at the proximal end prevents the stylet from passing all the way through the cannula. A small scalpel incision at the skin entrance of the mandrel 30 is made large enough to transmit the tandem multiple channel biopsy guide device 20. The guide channel 24 of the tandem multiple channel biopsy guide device 20 is slidably inserted over mandrel 30 until the biopsy channel 22 butts against the target 70. Up to this point, very common methods used widely for needle localization of non-palpable breast lesions have been described. The depth-penetration stop 40 is placed over the tandem multiple channel biopsy guide device 20 and is positioned against the skin 60. The set screw 42 on the depth-penetration stop 40 is then tightened. A mammogram is obtained providing a fourth image to confirm or adjust the proper relationship between the tandem multiple channel biopsy guide device 20 and the target lesion 70. The relationship is considered good when the guide cannula 24 transfixes the target lesion 70 and the biopsy cannula 22 is positioned apposed to the surface of target lesion 70 or alternatively at a specifically chosen depth within or next to target lesion 70.

If resistance to tissue passage of the tandem multiple channel biopsy device 20 is high, due to unusually firm breast tissue, the tissue dilator cannula temporarily slidably replaces the tandem multiple channel biopsy device 20 over the mandrel 30. The tissue dilator more effectively separates the breast tissues down to the level of target lesion 70 and provides the space through dense but normal breast tissue to advance the tandem multiple channel biopsy guide device 20 over the mandrel 30 into the target lesion 70. The stylet is then withdrawn. The desired appropriate tissue sampling apparatus is selected, armed and passed slidably inside the biopsy cannula 22 of the tandem multiple channel biopsy guide device 20 until tissue resistance is felt or until the pre-measured cannula length is reached. The tissue sampling apparatus is usually positioned just short of the target lesion 70, but it may be placed more deeply. The instructed manufacturer's procedure for the given tissue sampling apparatus is followed to obtain a tissue sample. Examples of such tissue sampling apparatuses are disclosed in U.S. Pat. No. 4,881,551 and U.S. Pat. No. 4,907,599, the disclosures of which are herein incorporated in their entireties by reference.

A spring-loaded gun (not shown) of the tissue sampling apparatus is fired, passing its biopsy stylet 76 and cutting cannula 75 through the target lesion 70 and cutting off and capturing a sample thereof. The tissue sampling apparatus with the biopsy stylet 76 and cutting cannula 75 is withdrawn and the sample removed and deposited in an appropriate container. The tandem multiple channel biopsy guide device 20 is twisted 20° to 180° about the axle formed by the mandrel 30 presenting a new portion of the target lesion 70 to the distal end of the biopsy channel 22 as shown in FIGS. 5A and B. The tissue sampling apparatus is reinserted and tissue sampling and retrieval procedures are repeated. Guided by the confidence that the target is internally transfixed at a depth documented on earlier clear images, these procedural steps can be repeated many times, by varying the rotational angle and the tandem multiple channel biopsy guide device 20 depth until the desired number of target lesion samples have been obtained. This method can be reliably performed even after the target image is obscured by bleeding.

Ramifications and variations on the positioning and percutaneous tissue biopsy method using the tandem multiple channel biopsy guide device 20 and guide mandrel 30 appear as device related alterations described previously are used and which only mildly alter the method. Such alterations are further set forth below.

A simple, straight, pointed, guide mandrel with a removable proximal hub is the basic guide pin design. Variations in materials, length, flexibility, diameter and shape of guide pins are anticipated and can be used for special conditions. Changes in anchor means from the J-hook anchor 32 are anticipated, such as corkscrew, threaded tip, split diverging tip, retractable barbed needles, or gaining visible anchor control of the distal mandrel by passing it completely through the target area and out the opposite side of the breast. The basic method describes an internally transfixing guide pin eccentric to the biopsy process. Actual attachment of the transfixing guide pin to a biopsy cannula or to the biopsy guide device itself or attachment of a guide channel to the biopsy guide device itself are anticipated.

Changes in configuration and/or joining methods of the separate channels for guidance and tissue interaction into one tandem multiple channel biopsy guide device are within the scope of the present invention, see FIGS. 4A through 4E. More than two cannulas; single cannula divided into multichannels by septae or external shaping; changes in materials; changes in length of one or another component cannula; changes in joining means (permanent or detachable) or use of spacers between cannulas; lumen diameter, long-axis relationships (non-parallel, curved); lumen cross-section changes; various end shapes; different materials are all envisioned as variations of the present invention.

Any suitable means for the biopsy channel cannula to follow the guide mandrel such as noose, gutter, clamps, permanent attachment, etc., can be employed.

Alternate methods of delivering or guiding both guide mandrel and tandem multiple channel biopsy guide device to the target (large tube, exposure by surgical incision, endoscopic visualization, radio transmission control, magnetism detection and other emerging imaging methods) are all variations which can be used to deploy a target transfixing guide mandrel with guide channel joined to an eccentric tandem biopsy channel.

One skilled in the art will see the broad scope of possible uses for a method employing a target transfixing guide mandrel with coaxial guide channel and an eccentric tandem biopsy channel positioned percutaneously using commonly available imaging guidance. Devices required for the method include a stiff hubless removable guide mandrel 30, with or without a J-hook distal anchor 32 and a multiple channel biopsy guide device 20 comprised of a tandem guide and biopsy channels solidly joined proximally and distally (external ends and subcutaneous ends).

The target is generally an area of suspicious internal tissue that is seen on medical imaging. The guide mandrel 30 holds the target in place throughout the procedure even in the face of patient movement. The mandrel also provides a rigid guide path through intervening normal non-target tissues to reach the target with the multiple channel biopsy guide device 20. When medical imaging guidance is by standard mammography, a first view directs the guide mandrel 30 parallel to the x-ray beam through the target 70. The second substantially perpendicular mammogram view provides the distance measurement for depth of penetration for the multiple channel biopsy guide device 20. The multiple channel biopsy guide device 20 is then deployed to the depth of the target by following one of its channels over the guide mandrel 30. The other channel provides for the biopsy, and is directly adjacent to (eccentric to; non-coaxial to;) the guide mandrel 30. A needle biopsy device of a separate manufacture is advanced slidably down the biopsy channel 24 and operates according to its manufacturer instructions to obtain multiple tissue samples from target 70 approximately 3 mm to 25 mm distal to the biopsy channel 24, rotating to any radial target location that is within 2 mm to 5 mm from the guide mandrel 30. The method associated with the mandrel and tandem multichannel biopsy guide device operates with the biopsy needle parallel to the compression paddle and film holder, unlike stereotactic biopsy needles that are directed substantially perpendicular to the compression paddle wherein stereotactic biopsies are limited in depth by the film holder under the breast. Only long-throw biopsy needles are used with the multiple channel biopsy guide device because there is no physical restriction to depth of penetration.

The biopsy guide device 20 is inexpensive to manufacture. Inventory costs and capital expenditures are reduced. The biopsy guide device 20 replaces expensive in-vogue stereotactic imaging equipment, and many open surgical breast biopsies. The biopsy guide device 20 uses widely distributed existing imaging equipment. The biopsy guide device 20 is inserted parallel to the image receptor plane instead of perpendicular. The biopsy guide device 20 follows widely applied medical techniques already in existence for other purposes. Tissue sampling is performed through a rigid cannula so the side pressure from breast compression does not impede the action of the cutting device mechanism. Single tissue penetration with the guide allows multiple biopsies. The probability of needle track seeding of intervening normal tissue with malignant cells or abscess bacteria is greatly reduced. The target will not be missed because of untimely patient movement. The target cannot slip off to the side during biopsy thrusts. The target can still be sampled even after bleeding obscures the target to further imaging. Simple rotation of the eccentric biopsy channel around the transfixing guide mandrel 30 allows the biopsy of a new portion of the target. There is no need to withdraw or re-use medical imaging to reposition the biopsy guide device for an additional specimen from a new part of the target.

The embodiment specified herein depicts an image-guided method to allow repeated tissue core biopsies of externally hidden, but image-detected, tissue targets. The multiple channel biopsy guide device 20 passes through normal intervening tissues only once at the beginning and again at the end of the procedure, regardless of the number of biopsies. Initial use will be for mammographic and sonographic guided breast biopsies, but the method is applicable to many medical imaging technologies and to many body parts, particularly for connective tissue and muscle targets.

As various possible embodiments may be made in the above invention for use for different purposes and various changes might be made in the embodiments and method above set forth, it is understood that all of the above matters here set forth or shown in the accompanying drawings are to be interpreted as illustrative and not limiting. Although the description above contains many specifications, these should not be construed as limiting the scope of the invention but as merely providing illustrations of the present preferred commercially pursuable embodiment. Thus, the scope of the invention should be determined by the appended claims.

What is claimed is:

1. A biopsy guide device comprising at least one means for receiving a biopsy obtaining instrument joined in tandem to a means for guiding the biopsy guide device to a target area, the biopsy guide device rotatable around the target area such that the biopsy obtaining instrument in the receiving means can obtain multiple biopsies at the target area without withdrawing said biopsy guide device from said target area.

2. The biopsy guide device of claim 1, wherein said at least one means for receiving the biopsy obtaining instrument comprises at least one cannula.

3. The biopsy guide device of claim 1, wherein the means for guiding the biopsy guide device to the target area comprises a guide cannula.

4. The biopsy guide device of claim 3, wherein the guide cannula comprises a guide mandrel movable within said cannula.

5. The biopsy guide device of claim 4 wherein the guide mandrel comprises a J-hook, a Y-hook, or is threaded, spiral, or aciculate at the distal end of the mandrel.

6. The biopsy guide device of claim 2, wherein said biopsy obtaining instrument comprises a biopsy needle movable through said cannula for obtaining a specimen at the target area.

7. The biopsy guide device of claim 1, further comprising a depth-penetration stop joined proximal to the means for receiving the biopsy obtaining instrument and the means for guiding the biopsy guide device to the target area to control the depth-penetration of the biopsy guide device to the target area.

8. The biopsy guide device of claim 4, wherein said means for receiving the biopsy obtaining instrument and said guide cannula are rotatable around said guide mandrel when at least a portion of said guide mandrel is contained within said guide cannula.

9. The biopsy guide device of claim 4, wherein said guide mandrel secures the biopsy guide device to the target area and said means for receiving the biopsy obtaining instrument is rotatable around said guide mandrel.

10. The biopsy guide device of claim 1, wherein the means for receiving the biopsy obtaining instrument is joined to the guiding means by a mechanical spacer.

11. The biopsy guide device of claim 1 wherein the means for receiving the biopsy obtaining instrument is joined to the guiding means by an adhesive or weld.

12. The biopsy guide device of claim 2, wherein said means for guiding the biopsy guide device comprises a guide cannula and a guide mandrel movable within said guide cannula, said at least one cannula for receiving the biopsy obtaining instrument and said guide cannula being rotatable around said guide mandrel.

13. The biopsy guide device of claim 12 wherein said at least one cannula for receiving the biopsy obtaining instrument is joined to said guide cannula by means of an adhesive, weld or by a mechanical spacer means.

14. The biopsy guide device of claim 12, wherein said guide mandrel has a J-hook, a Y-hook, or a threaded, a spiral, or an aciculate distal end to secure the biopsy guide device to the target area.

15. The biopsy guide device of claim 12, wherein said biopsy obtaining instrument includes a biopsy needle movable through said at least one cannula for obtaining a specimen from the target area.

16. A method for positioning a biopsy guide device and obtaining a biopsy at a subcutaneous target area comprising:

providing a biopsy guide device comprising at least one means for receiving a biopsy obtaining instrument joined in tandem to a means for guiding the biopsy guide device to the target area, the biopsy guide device rotatable around the target area such that the biopsy obtaining instrument can obtain multiple biopsies without withdrawing said biopsy guide device from said target area;

guiding the biopsy guide device to a first location of the subcutaneous target area and securing the biopsy guide device to the target area by internally transfixing the subcutaneous target area with the guiding means of the biopsy guide device;

contacting the subcutaneous target area with the at least one means for receiving the biopsy obtaining instrument; and obtaining at least one biopsy at said first location of the subcutaneous target area with the biopsy obtaining instrument.

17. The method of claim 16, further comprising the step of rotating the biopsy guide device around an axis of the biopsy guiding means to a second location at the subcutaneous target area without withdrawing said biopsy guide device from said target area and obtaining an additional biopsy at said second location.

18. The method of claim 16, wherein the means for guiding the biopsy guide device to the target area comprises a guide cannula and a guide mandrel movable in said guide cannula, and wherein securing the biopsy guide device at said first location of the subcutaneous target area comprises first fixing said guide mandrel at said target area, placing said guide cannula over said guide mandrel and forwarding said biopsy guide device over said guide mandrel to said first location.

19. The method of claim 18, wherein said means for receiving the biopsy obtaining instrument is a biopsy cannula and said biopsy obtaining instrument comprises a biopsy needle movable through said biopsy cannula and said biopsy is obtained by directing said biopsy needle through said biopsy cannula when said biopsy guide device is forwarded at said first location.

20. The method of claim 18 wherein said subcutaneous target area is found by an imaging process.

21. The method of claim 20 wherein said imaging process is x-ray imaging.

* * * * *